(12) United States Patent
Ong et al.

(10) Patent No.: US 8,507,746 B2
(45) Date of Patent: Aug. 13, 2013

(54) LEAKAGE-SIGNALING ABSORBENT ARTICLE

(75) Inventors: Yein Sze Ong, Singapore (SG); Meijia Ng, Singapore (SG); Eng Choo Priscilla Goh, Maplewoods (SG); Cheng Kwee Ling, Singapore (SG); Doo Hong Kim, Makati City (PH); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 431 days.

(21) Appl. No.: 12/316,683

(22) Filed: Dec. 16, 2008

(65) Prior Publication Data

US 2010/0152690 A1 Jun. 17, 2010

(51) Int. Cl.
*A61F 13/15* (2006.01)

(52) U.S. Cl.
USPC ............................................... 604/361

(58) Field of Classification Search
USPC ............................ 604/385.01, 361
See application file for complete search history.

(56) References Cited

U.S. PATENT DOCUMENTS

| | | | |
|---|---|---|---|
| 2,681,032 A | 6/1954 | Shaw | |
| 3,338,992 A | 8/1967 | Kinney | |
| 3,341,394 A | 9/1967 | Kinney | |
| 3,371,668 A | 3/1968 | Johnson | |
| 3,502,538 A | 3/1970 | Petersen | |
| 3,502,763 A | 3/1970 | Hartmann | |
| 3,542,615 A | 11/1970 | Dobo et al. | |
| 3,556,932 A | 1/1971 | Coscia et al. | |
| 3,556,933 A | 1/1971 | Williams et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,246,900 A | 1/1981 | Schroder | |
| 4,340,563 A | 7/1982 | Appel et al. | |
| 4,357,938 A | 11/1982 | Ito et al. | |
| 4,418,524 A * | 12/1983 | Ito et al. | ........................... 57/239 |
| 4,447,240 A | 5/1984 | Ito et al. | |
| 4,488,928 A | 12/1984 | Ali Khan et al. | |
| 4,623,342 A | 11/1986 | Ito et al. | |
| 4,640,859 A | 2/1987 | Hansen et al. | |
| 4,675,394 A | 6/1987 | Solarek et al. | |

(Continued)

FOREIGN PATENT DOCUMENTS

| | | |
|---|---|---|
| CN | D 3251084 | 8/2002 |
| EP | 0 220 741 A2 | 5/1987 |

(Continued)

*Primary Examiner* — Jackie Ho
*Assistant Examiner* — Bradley Philips
(74) *Attorney, Agent, or Firm* — Randall w. Fieldhack

(57) ABSTRACT

An absorbent article for preventing leakage is provided, the article including an absorbent assembly having an absorbent assembly perimeter, and a leakage warning element disposed adjacent a portion of the perimeter, wherein the leakage warning element includes a dimension change member adapted to dimensionally change upon liquid contact to produce a transition in the absorbent article between an activated state and an un-activated state, thereby producing a physical sensation indicating a fullness level of the absorbent assembly. The absorbent article also provides an absorbent assembly having an absorbent assembly perimeter and a leakage warning element including a stored energy device and a dimension change member, the dimension change member disposed along a portion of the perimeter, wherein the dimension change member is adapted to break upon liquid contact to produce a transition in the leakage warning element from an un-activated state to an activated state.

19 Claims, 4 Drawing Sheets

(56) References Cited

U.S. PATENT DOCUMENTS

| | | | |
|---|---|---|---|
| 4,779,456 | A | 10/1988 | Cantoni |
| 4,781,731 | A | 11/1988 | Schlinger |
| 4,787,896 | A | 11/1988 | Houghton et al. |
| 4,809,493 | A | 3/1989 | Genba et al. |
| 4,834,733 | A * | 5/1989 | Huntoon et al. ............... 604/361 |
| 4,911,701 | A | 3/1990 | Mavinkurve |
| 4,981,557 | A | 1/1991 | Bjorkquist |
| 5,007,906 | A | 4/1991 | Osborn, III et al. |
| 5,008,344 | A | 4/1991 | Bjorkquist |
| 5,085,736 | A | 2/1992 | Bjorkquist |
| 5,122,407 | A | 6/1992 | Yeo et al. |
| 5,160,331 | A | 11/1992 | Forester et al. |
| 5,176,672 | A | 1/1993 | Bruemmer et al. |
| 5,181,563 | A | 1/1993 | Amaral |
| 5,260,345 | A | 11/1993 | Desmarais et al. |
| 5,330,598 | A | 7/1994 | Erdman et al. |
| 5,334,176 | A | 8/1994 | Buenger et al. |
| 5,397,316 | A | 3/1995 | LaVon et al. |
| 5,415,640 | A | 5/1995 | Kirby et al. |
| 5,447,507 | A | 9/1995 | Yamamoto |
| 5,514,121 | A | 5/1996 | Roe et al. |
| 5,520,674 | A | 5/1996 | Lavon et al. |
| 5,527,303 | A | 6/1996 | Milby, Jr. et al. |
| 5,575,785 | A | 11/1996 | Gryskiewicz et al. |
| 5,591,150 | A | 1/1997 | Olsen et al. |
| 5,779,860 | A | 7/1998 | Hollenberg et al. |
| 5,833,680 | A | 11/1998 | Hartman |
| 5,858,515 | A | 1/1999 | Stokes et al. |
| 5,885,264 | A | 3/1999 | Matsushita |
| 5,997,520 | A | 12/1999 | Ahr et al. |
| 6,045,900 | A | 4/2000 | Haffner et al. |
| 6,071,580 | A | 6/2000 | Bland et al. |
| 6,114,597 | A | 9/2000 | Romare |
| 6,133,501 | A | 10/2000 | Hallock et al. |
| 6,168,583 | B1 | 1/2001 | Tanji et al. |
| 6,175,056 | B1 | 1/2001 | Carlucci et al. |
| D448,476 | S | 9/2001 | Page et al. |
| 6,293,935 | B1 | 9/2001 | Kimura et al. |
| D448,846 | S | 10/2001 | Page et al. |
| 6,296,628 | B1 | 10/2001 | Mizutani |
| 6,306,818 | B1 | 10/2001 | Anderson et al. |
| 6,315,765 | B1 | 11/2001 | Datta et al. |
| 6,326,525 | B1 | 12/2001 | Hamajima et al. |
| 6,346,097 | B1 | 2/2002 | Blaney |
| 6,348,047 | B1 | 2/2002 | Harper |
| 6,387,084 | B1 | 5/2002 | VanGompel et al. |
| 6,392,117 | B1 | 5/2002 | Mayer et al. |
| 6,429,261 | B1 | 8/2002 | Lang et al. |
| 6,432,097 | B1 * | 8/2002 | Ahr et al. ................. 604/385.19 |
| 6,436,081 | B1 | 8/2002 | Wada et al. |
| 6,444,214 | B1 | 9/2002 | Cole et al. |
| 6,521,811 | B1 | 2/2003 | Lassen et al. |
| 6,537,663 | B1 | 3/2003 | Chang et al. |
| 6,548,592 | B1 | 4/2003 | Lang et al. |
| 6,551,297 | B2 | 4/2003 | Tanaka et al. |
| 6,579,570 | B1 | 6/2003 | Lang et al. |
| 6,585,712 | B2 | 7/2003 | Yoshimasa |
| 6,599,848 | B1 | 7/2003 | Chen et al. |
| 6,620,144 | B1 | 9/2003 | Glasgow et al. |
| 6,627,670 | B2 | 9/2003 | Mork et al. |
| 6,632,205 | B1 | 10/2003 | Sauer |
| 6,653,406 | B1 | 11/2003 | Soerens et al. |
| 6,664,436 | B2 | 12/2003 | Topolkaraev et al. |
| 6,666,850 | B1 | 12/2003 | Ahr et al. |
| 6,683,143 | B1 | 1/2004 | Mumick et al. |
| 6,713,414 | B1 | 3/2004 | Pomplun et al. |
| 6,727,004 | B2 | 4/2004 | Goulet et al. |
| 6,761,709 | B2 * | 7/2004 | Morman et al. ....... 604/385.101 |
| 6,786,893 | B2 | 9/2004 | Strand |
| 6,815,502 | B1 | 11/2004 | Lang et al. |
| 6,840,925 | B2 | 1/2005 | Mishima et al. |
| 6,908,458 | B1 | 6/2005 | Sauer et al. |
| 6,958,430 | B1 | 10/2005 | Marinelli |
| D521,149 | S | 5/2006 | Adams et al. |
| 7,037,298 | B2 | 5/2006 | Ohshima et al. |
| 7,083,604 | B2 | 8/2006 | Sakaguchi |
| 7,145,054 | B2 | 12/2006 | Zander et al. |
| 7,176,344 | B2 * | 2/2007 | Gustafson et al. ............ 604/361 |
| 7,179,247 | B2 | 2/2007 | Mizutani et al. |
| 7,252,870 | B2 | 8/2007 | Anderson et al. |
| 7,314,967 | B2 | 1/2008 | Ashton et al. |
| D567,369 | S | 4/2008 | Gilroy |
| 7,358,282 | B2 | 4/2008 | Krueger et al. |
| 7,491,864 | B2 | 2/2009 | Nishizawa et al. |
| D600,802 | S | 9/2009 | Hood et al. |
| D600,803 | S | 9/2009 | Hood et al. |
| D600,805 | S | 9/2009 | Hood et al. |
| 7,621,899 | B2 | 11/2009 | Fujikawa et al. |
| 7,847,145 | B2 | 12/2010 | Kurita et al. |
| 2001/0029359 | A1 | 10/2001 | Carlucci |
| 2002/0128625 | A1 | 9/2002 | Tanaka et al. |
| 2003/0050614 | A1 | 3/2003 | D'Acchioli et al. |
| 2003/0163104 | A1 | 8/2003 | Tears et al. |
| 2005/0010185 | A1 | 1/2005 | Mizutani et al. |
| 2005/0124956 | A1 | 6/2005 | Suzuki |
| 2006/0116651 | A1 | 6/2006 | Kurita et al. |
| 2006/0148917 | A1 | 7/2006 | Radwanski et al. |
| 2006/0246272 | A1 | 11/2006 | Zhang et al. |
| 2006/0282059 | A1 | 12/2006 | Fujikawa et al. |
| 2006/0287635 | A1 | 12/2006 | Angel |
| 2007/0043027 | A1 | 2/2007 | Rueckle et al. |
| 2007/0093772 | A1 | 4/2007 | Koyama et al. |
| 2007/0225671 | A1 | 9/2007 | Angel |
| 2007/0287973 | A1 | 12/2007 | Cohen et al. |
| 2008/0065035 | A1 | 3/2008 | Perneborn |
| 2008/0269703 | A1 | 10/2008 | Collins et al. |
| 2009/0036854 | A1 | 2/2009 | Guidotti et al. |
| 2009/0054760 | A1 | 2/2009 | Burke |
| 2009/0054860 | A1 | 2/2009 | Young et al. |
| 2009/0157022 | A1 | 6/2009 | MacDonald et al. |
| 2009/0157032 | A1 | 6/2009 | MacDonald et al. |
| 2009/0204095 | A1 | 8/2009 | McDaniel |
| 2009/0240220 | A1 | 9/2009 | MacDonald et al. |
| 2009/0299312 | A1 | 12/2009 | MacDonald et al. |
| 2009/0326495 | A1 | 12/2009 | MacDonald et al. |
| 2010/0147203 | A1 | 6/2010 | MacDonald et al. |
| 2010/0152642 | A1 | 6/2010 | Kim et al. |
| 2010/0152692 | A1 | 6/2010 | Ong et al. |

FOREIGN PATENT DOCUMENTS

| | | |
|---|---|---|
| EP | 0 554 565 A1 | 8/1993 |
| EP | 0 557 047 A1 | 8/1993 |
| EP | 0 815 816 A1 | 1/1998 |
| EP | 0 815 821 A2 | 1/1998 |
| EP | 0 846 454 A1 | 6/1998 |
| EP | 1 206 923 A1 | 5/2002 |
| EP | 000772975-0028 | 11/2008 |
| GB | 2 244 653 A | 12/1991 |
| GB | D2 078 590 | 2/1999 |
| JP | 02-107249 A | 4/1990 |
| JP | 03-185197 A | 8/1991 |
| JP | 2001-017467 A | 1/2001 |
| JP | 2004-041339 A | 2/2004 |
| JP | 1233575 S | 3/2005 |
| JP | 2006-334113 A | 12/2006 |
| JP | 1318295 S | 12/2007 |
| WO | WO 94/02095 | 2/1994 |
| WO | WO 95/25493 | 9/1995 |
| WO | WO 97/14389 A1 | 4/1997 |
| WO | WO 97/40798 A1 | 11/1997 |
| WO | WO 97/40803 A1 | 11/1997 |
| WO | WO 97/46185 A1 | 12/1997 |
| WO | WO 00/00145 A2 | 1/2000 |
| WO | WO 00/53830 A1 | 9/2000 |
| WO | WO 2005/016103 A1 | 2/2005 |
| WO | WO 2006/021763 A1 | 3/2006 |
| WO | WO 2007/073254 A1 | 6/2007 |
| WO | WO 2007/125352 A1 | 11/2007 |

* cited by examiner

LEAKAGE-SIGNALING ABSORBENT ARTICLE

BACKGROUND

The present disclosure relates to absorbent articles that include a leakage warning element. More specifically, the disclosure relates to an absorbent article such as feminine care products, incontinence products, and training pants that provides the wearer with a noticeable physical sensation when the absorbent article is reaching fullness or to protect against sudden fluid gushes to the edge of the pad, and prior to potential leakage from the absorbent article.

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, it can reduce the wearer's ability to notice or recognize when the article is becoming full, especially if the wearer's attention is distracted by an activity. In one example, all adult care wearers, especially women, are very concerned about leakage in public. Some wearers can be so bothered by leakage that if it occurs in a public place, they will avoid that place and situation for the rest of their life. Leakage is therefore absolutely taboo in an adult care product.

Similarly, leakage from catamenial products poses a major problem to women and can be a social embarrassment, especially if it happens in public places. Current products exist that can delay or minimize leakage through length extension, material use, etc. There exist, however, situations in which women unknowingly wear catamenial products beyond leakage points and risk staining their clothes. A woman might also make several trips to the bathroom to check her pad for fear of leakage. Such behavior can make menstruation a more inconvenient experience than it needs to be.

The present disclosure teaches products and methods to sense and inform an absorbent article wearer when leakage is about to occur so that the absorbent article wearer can reliably avoid leakage.

SUMMARY

In response to the discussed deficiencies in the prior art, a new absorbent article has been developed. Absorbent articles of the present disclosure provide a physical sensation upon contact with menstrual fluid or other body exudates once the menstrual fluid or other body exudates has nearly filled the absorbent article. As a result, the wearer will notice a distinct physical sensation to assist the wearer in recognizing when the absorbent article is nearing fullness.

In one aspect of the present disclosure, an absorbent article for preventing leakage includes an absorbent assembly having an absorbent assembly perimeter and a leakage warning element disposed adjacent a portion of the perimeter, wherein the leakage warning element includes a dimension change member adapted to dimensionally change upon liquid contact to produce a transition in the absorbent article between an activated state and an un-activated state, thereby producing a physical sensation indicating a fullness level of the absorbent assembly.

In another aspect of the present disclosure, an absorbent article for signaling imminence of leakage from the absorbent article provides an absorbent assembly having an absorbent assembly perimeter, and a leakage warning element including a stored energy device and a dimension change member, the dimension change member disposed along a portion of the perimeter, wherein the dimension change member is adapted to break upon liquid contact to produce a transition in the leakage warning element from an un-activated state to an activated state, thereby producing a physical sensation indicating that leakage is imminent from the absorbent assembly.

In another aspect of the present disclosure, an absorbent article for signaling imminence of leakage from the absorbent article provides an absorbent assembly having an absorbent assembly perimeter, and a leakage warning element including a signaling flap and a dimension change member, the dimension change member disposed along a portion of the perimeter, wherein the dimension change member is adapted to shorten upon liquid contact to produce a transition in the leakage warning element from an un-activated state to an activated state, thereby producing a physical sensation indicating that leakage is imminent from the absorbent assembly.

The purposes and features of the present disclosure will be set forth in the description that follows. Additional features of the disclosure can be realized and attained by the product and processes particularly pointed out in the written description and claims hereof, as well as from the appended drawings.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
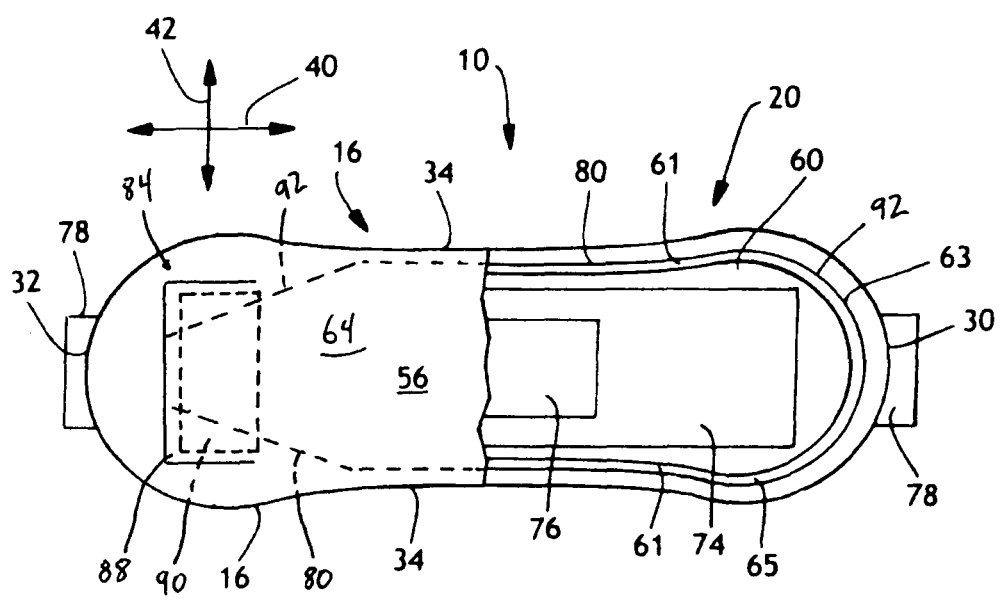
FIG. 1 representatively illustrates a partially cutaway plan view of a leakage warning system of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DEFINITIONS

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end wearer.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material can also include other materials, such as superabsorbent materials. The meltblown fibers and absorbent fibers are collected on a forming surface, such as provided by a foraminous belt. The forming surface can include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

"Disposable" refers to articles that are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

"Extensible" refers to a material or composite that is capable of extension or deformation without breaking, but does not substantially recover its original size and shape after removal of a force causing the extension or deformation. Suitably, an extensible material or composite can be elongated by at least 50 percent (to 150 percent) of its relaxed length.

"Fiber" refers to a continuous or discontinuous member having a high ratio of length to diameter or width. Thus, a fiber can be a filament, a thread, a strand, a yarn, or any other member or combination of these members.

"Hydrophilic" describes fibers or the surfaces of fibers that are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements. "Join" and its derivatives include permanent, releasable, or refastenable joinder. In addition, the joining can be completed either during the manufacturing process or by the end wearer.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Such a process is disclosed, for example, in U.S. Pat. No. 3,849,241 to Butin et al. Meltblown fibers can be continuous or discontinuous and are generally self bonding when deposited onto a collecting surface.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms can be defined with additional language in the remaining portions of the specification.

DETAILED DESCRIPTION

Figure 2:
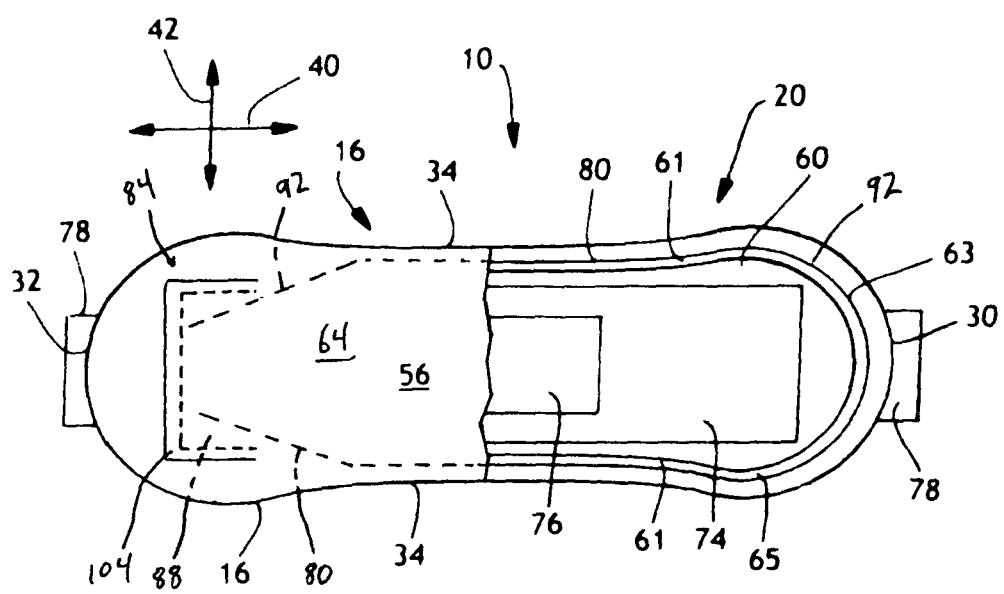
FIG. 2 representatively illustrates a partially cutaway plan view of another aspect of the leakage warning system of the present disclosure.
Figure 3:
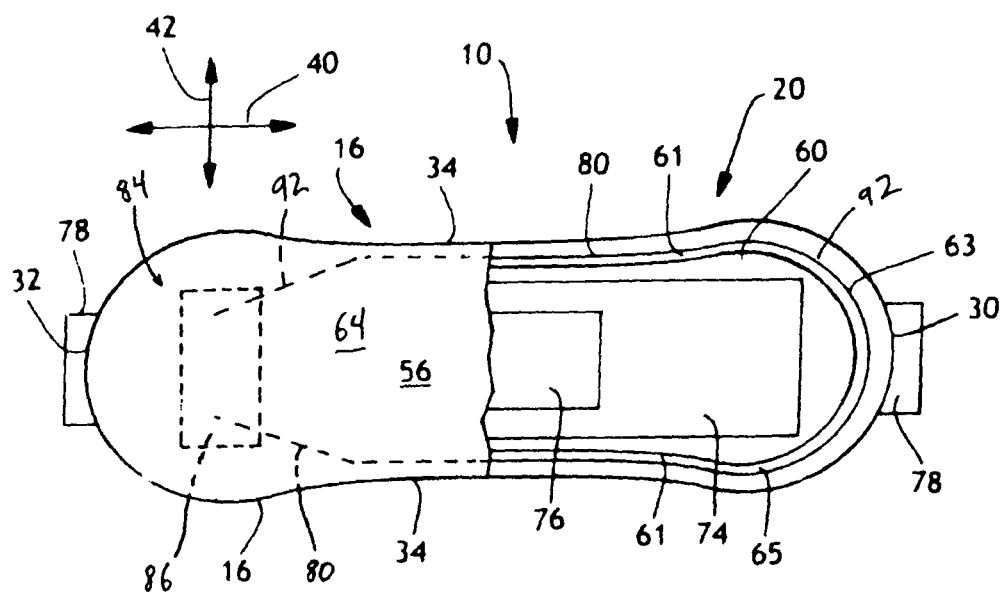
FIG. 3 representatively illustrates a partially cutaway plan view of still another aspect of the leakage warning system of the present disclosure including a stored energy device.

Referring now to the drawings and in particular to FIGS. 1-3, an absorbent article 10 of the present disclosure is representatively illustrated in the form of a feminine care pad and is indicated in its entirety by the reference numeral 16. The absorbent article 10 includes a leakage warning element 20 that is adapted to create a distinct physical sensation to the wearer upon the absorbent article 10 nearing fullness, which can enhance a wearer's ability to recognize when leakage can be a threat.

While a leakage warning element 20 is illustrated in FIGS. 1-3 with a feminine care pad 16, the leakage warning element 20 can also be used in conjunction with other garments. For example, a leakage warning element 20 of the disclosure can be used with other disposable absorbent articles such as diapers, diaper pants, training pants, incontinence articles, feminine liners and tampons, or the like. The descriptions of the various absorbent articles 10 described herein are for exemplary purposes only. Variations in the structures, materials, and designs of the absorbent articles 10 that do not impact the subject matter of this disclosure are possible and expected.

As noted previously, the leakage warning element 20 is positioned and adapted to create a distinct physical sensation upon the absorbent article 10 approaching fullness. As the absorbent assembly 60 fills with menstrual fluid or other body exudates, the menstrual fluid or other body exudates wicks onto the leakage warning element 20 where the menstrual fluid or other body exudates initiates a physical sensation that can be felt by the wearer of the absorbent article 10, thus alerting the wearer that a leak can soon occur.

The leakage warning element 20 is also positioned and adapted to create a distinct physical sensation to protect against sudden fluid gushes to the edge of the pad. Such gushes usually remain near the top surface of the absorbent article 10 and do not have sufficient time to get into the absorbent assembly 60. A gush can be caused by several factors including an insufficient fluid intake rate for the body side liner material. These fluid gushes can sometimes cause leakage even if the pad is not near its full capacity.

The present disclosure can be applied to a feminine/incontinence pad 16, as illustrated in FIGS. 1-3. The exemplary feminine/incontinence pad 16 includes an outercover (otherwise referred to as a baffle or backsheet, not shown), an absorbent assembly 60, an optional tissue layer 74, an optional distribution layer (surge layer) 76 and a bodyside liner 64 (also referred to as the topsheet). The feminine/incontinence pad 16 also has first and second side edges 34 that are the longitudinal sides of the elongated feminine/incontinence pad 16. The side edges 34 can be contoured, for example, in a concave shape, or they can be linear. The sides can further include extensions that extend laterally outward. Extensions are known in the art (sometimes as flaps or wings) and are shown in, for example U.S. Pat. No. 6,387,084 issued to VanGompel et al., the contents of which are incorporated herein by reference to the extent that they are consistent (i.e., not in conflict) herewith. In one aspect (not shown), one or more elastic elements are disposed along the sides to form a gasket with the body of the wearer. Elastic sides are known in the art, as is shown in U.S. Pat. No. 6,315,765 issued to Datta et al., the contents of which are incorporated herein by reference to the extent that they are consistent (i.e., not in conflict) herewith. In one aspect, the elastic elements are disposed between the bodyside liner 64 and the outercover.

The feminine/incontinence pad 16 has a bodyside inner surface 56 and a garment-side outer surface (not shown). Applied to at least a portion of the garment-side outer surface is a garment attachment adhesive. In various aspects, the garment attachment adhesive is configured as a single band of adhesive or as two or more spaced apart strips. Alternatively, the garment attachment adhesive can include a swirl pattern of adhesive that encompasses a major portion of the garment-side outer surface of the feminine/incontinence pad 16.

A release strip 78, also known as a releasable peel strip, is removably secured to the garment attachment adhesive and serves to prevent premature contamination of the adhesive before the feminine/incontinence pad 16 is secured to the crotch portion of an undergarment. In various aspects, the garment attachment adhesive is designed to be secured to the inner crotch portion of an undergarment so as to keep the absorbent product in register with the body of the wearer. The release strip 78 can extend beyond one or both of the end edges 30, 32 of the outercover, as shown in FIG. 1. Alternatively, the release strip 78 can be as short as the length of the garment attachment adhesive, or slightly longer than the adhesive or can be only as long as the garment attachment adhesive, but does not extend beyond the end edges 30, 32 of the outercover.

The bodyside liner or topsheet 64, which is preferably liquid permeable, can be formed from one or more materials. The bodyside liner or topsheet 64 must be able to manage different body excretions depending on the type of product. In feminine care products, often the bodyside liner or body-contacting layer 64 must be able to handle menses and urine. In the present disclosure, the bodyside liner or topsheet 64 can include a layer constructed of any operative material, and can be a composite material. For example, the bodyside liner or body-contacting layer 64 can include a woven fabric, a nonwoven fabric, a polymer film, a film-nonwoven fabric laminate or the like, as well as combinations thereof. Examples of a nonwoven fabric useable in the bodyside liner or topsheet 64 include, for example, an airlaid nonwoven web, a spunbond nonwoven web, a meltblown nonwoven web, a bonded-carded-web, a hydroentangled nonwoven web, a spunlace web or the like, as well as combinations thereof. Other examples of suitable materials for constructing the bodyside liner or topsheet 64 can include rayon, bonded-carded-webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials.

Other examples of suitable materials for the bodyside liner or topsheet 64 are composite materials of a polymer and a nonwoven fabric material. The composite materials are typically in the form of integral sheets generally formed by the extrusion of a polymer onto a nonwoven web, such as a spunbond material. In a desired arrangement, the liner or body contacting layer 64 can be configured to be operatively liquid-permeable with regard to the liquids that the article is intended to absorb or otherwise handle. The operative liquid-permeability can, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent assembly 60). The selected arrangement of liquid-permeability is desirably present at least on an operative portion of the bodyside liner or topsheet 64 that is appointed for placement on the bodyside of the article. The bodyside liner or topsheet 64 can provide comfort and conformability, and can function to direct bodily exudates away from the body and toward the absorbent assembly 60. The bodyside liner or topsheet 64 can be configured to retain little or no liquid in its structure, and can be configured to provide a relatively comfortable and non-irritating surface next to the body tissues of a wearer. In the present disclosure, the topsheet or body-facing surface of each absorbent article can be embossed, printed, or otherwise imparted with a pattern.

The outercover can include a layer constructed of any operative material, and can have a selected level of liquid-permeability or liquid-impermeability, as desired. In a particular configuration, the outercover can be configured to provide an operatively liquid-impermeable baffle structure. The outercover can, for example, include a polymeric film, a woven fabric, a nonwoven fabric or the like, as well as combinations or composites thereof. For example, the outercover can include a polymer film laminated to a woven or nonwoven fabric. In a particular feature, the polymer film can be composed of polyethylene, polypropylene, polyester or the like, as well as combinations thereof. Additionally, the polymer film can be micro-embossed, have a printed design, have a printed message to the consumer, and/or can be at least partially colored. Suitably, the outercover can operatively permit a sufficient passage of air and moisture vapor out of the article, particularly out of an absorbent (e.g. storage or absorbent assembly 60) while blocking the passage of bodily liquids. An example of a suitable outercover material can include a breathable, microporous film, such as those described in, for example, U.S. Pat. No. 6,045,900 to McCormack et al.

Bicomponent films or other multi-component films can also be used, as well as woven and/or nonwoven fabrics that have been treated to render them operatively liquid-impermeable. Another suitable outercover material can include closed-cell polyolefin foam. For example, closed-cell polyethylene foam can be employed.

The liquid permeable bodyside liner 64 and the liquid-impermeable outercover can be peripherally sealed together to enclose the absorbent assembly 60 to form the feminine/incontinence pad 16. Alternatively, the bodyside liner or topsheet 64 can be wrapped around both the absorbent assembly 60 and the outercover to form a wrapped pad. The bodyside liner 64 and outercover, and other components of the feminine/incontinence pad 16, can be joined for example with adhesive bonds, sonic bonds, thermal bonds, pinning, stitching or any other attachment techniques known in the art, as well as combinations thereof.

The absorbent assembly 60 can be in a variety of shapes and configurations as are known in the art, such as rectangular, hourglass shaped, I-shaped, and the like. The absorbent assembly 60 has opposed lateral edges 61 and opposed longitudinal ends 63. The lateral edges 61 and longitudinal ends 63 together make up the perimeter 65 of the absorbent assembly 60.

The absorbent assembly 60 is designed to absorb body exudates, including menstrual fluid, blood, urine, and other body fluids. The absorbent assembly 60 can contain one or more layers of absorbent material. The layers can contain similar materials or different materials. Suitable materials for the absorbent assembly 60 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has good absorbency.

The absorbent assembly 60 can also be formed from a composite including a hydrophilic material that can be formed from various natural or synthetic fibers, wood pulp fibers, regenerated cellulose or cotton fibers, or a blend of pulp and other fibers. A desired material is an airlaid material.

In one aspect, the absorbent assembly 60 also includes a superabsorbent material, in addition to or in place of the hydrophilic material, that increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material can be biodegradable or bipolar. The hydrogel-forming polymeric absorbent material can be formed from organic hydrogel-forming polymeric material, which can include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers can be lightly crosslinked to render the material substantially water insoluble. Crosslinking can, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency-under-load value above 25 grams of absorbed liquid per gram of absorbent material (g/g). Other types of superabsorbent materials known to those skilled in the art can also be used.

Additional layers or substrates, including for example, the liquid acquisition and distribution layer 76, also referred to as a surge or transfer layer, and an optional tissue layer 74 can also be incorporated into the feminine/incontinence pad 16.

The leakage warning element 20 is positioned within the feminine/incontinence pad 16 so that menstrual fluid or other body exudates filling the absorbent assembly 60 contacts the leakage warning element 20 prior to completely filling and eventually leaking from the feminine/incontinence pad 16. Thus, the leakage warning element 20 is disposed with or near the absorbent assembly 60 so that menstrual fluid or other body exudates contacting the absorbent assembly will also eventually contact the leakage warning element 20. Most desirably, the leakage warning element 20 is disposed on the bodyside of the absorbent assembly 60 so as to be sandwiched between the absorbent assembly 60 and the bodyside liner 64. In this way, the physical sensation resulting from the leakage warning element 20 is more easily noticed by the wearer.

Alternatively, however, the leakage warning element 20 can be located within the absorbent assembly 60 or beneath the absorbent assembly 60 (not shown). The leakage warning element 20 can also be positioned on the extensions or in any other suitable position in the feminine/incontinence pad 16, as long as fluid communication is provided between the absorbent assembly 60 and the leakage warning element 20. In addition, leakage warning elements 20 can be positioned in more than one location within the feminine/incontinence pad 16. The leakage warning element 20 can be bonded in position using adhesives, ultrasonic bonds, or other suitable means.

One or more leakage warning elements 20 can be disposed with the feminine/incontinence pad 16. A pair of leakage warning elements 20 can be positioned on opposite sides of the longitudinal axis 40 and spaced apart from the intersection of the longitudinal and transverse axes 40, 42 along the transverse axis 42. Similarly, a pair of leakage warning elements 20 can be positioned on opposite sides of the transverse axis 42 and spaced apart from the intersection of the longitudinal and transverse axes 40, 42 along the longitudinal axis 40. In another aspect, leakage warning elements 20 can be positioned at each of the points at which an axis meets the perimeter 65 of the absorbent assembly 60. In still another aspect, the leakage warning elements 20 can be positioned completely or partially along the entire absorbent assembly perimeter 65.

The position and/or structure of the leakage warning elements 20 should be such that the leakage warning elements 20 come in contact with menstrual fluid or other bodily waste as the absorbent assembly 60 fills but prior to any leakage from the absorbent assembly 60. The leakage warning element(s) 20 can be centered in the longitudinal direction 40. Alternatively, however, the leakage warning element(s) 20 can be located off the transverse axis 40 of the feminine/incontinence pad 16. Likewise, the leakage warning element(s) 20 can be centered in the transverse direction 42 or can be located off the longitudinal axis 42 of the feminine/incontinence pad 16.

The leakage warning element 20 generally includes a dimension change member 80 connected to a reactive component 84. The dimension change member 80 changes at least one dimension when exposed to menstrual fluid or other bodily exudate. The dimension change member 80 includes a material or materials that rapidly undergo a change in at least one dimension when exposed to an aqueous solution. The change in dimension results in the reactive component 84 reacting by moving or by enabling movement.

In one aspect illustrated in FIGS. 3-5B, the dimension change member 80 includes a transformational string 92 that breaks upon exposure to menstrual fluid or other bodily exudate and releases the reactive component 84, which can include a stored energy device 86 such as a spring-like element. The release of the stored energy device 86 can cause part or all of the stored energy device 86 to move or translate to a different position. In this aspect, either the stored energy device 86 itself provides a physical sensation to the wearer of the absorbent article 10, or the movement of the stored energy device 86 influences another portion of the absorbent article 10 to provide the physical sensation to the wearer.

In another aspect illustrated in FIGS. 1-2, the transformational string 92 shortens upon exposure to menstrual fluid or other bodily exudate and pulls on the reactive component 84, which can include a signaling flap 88. The pull on the signaling flap 88 causes the signaling flap 88 to move or translate to a different position. In this aspect, either the signaling flap 88 itself provides a physical sensation to the wearer of the absorbent article, or the movement of the signaling flap 88 reveals a textured or other similar surface 90 that had previously been covered by the signaling flap 88 and that provides the physical sensation to the wearer.

In the aspect in which the transformational string 92 breaks upon exposure to menstrual fluid or other bodily exudate, the dimension change member 80 can include a water-soluble transformational string 92 including polyvinyl alcohol (PVA). Transformational string 92 made from water-soluble PVA has great tensile strength and only displays weakness when it comes into contact with moisture or water. A very small amount of water is required for complete dissolution of this material. The transformational string 92, upon exposure to menstrual fluid or other bodily exudate, will break, which can include dissolving, thus limiting the influence of the transformational string 92 in restraining the stored energy device 86. Sources of suitable transformational string 92 include Nitivy Company Limited, Japan (www.nitivy.co.jp/english/index.html).

Returning to FIGS. 3-5B, the transformational string 92 is positioned around the perimeter 65 of the absorbent article 10; tension in the transformational string 92 holds the stored energy device 86 in an un-activated state. The stored energy device 86 can be placed at the back end of the absorbent article 10, where there is sufficient space for the stored energy device 86 to move upon activation. When menstrual fluid or other bodily exudate soaks up the pad or gushes to the edge of the pad and contacts any point on the transformational string 92, the transformational string 92 dissolves, distends, and/or breaks (collectively referred to herein as breaking), resulting in a loss of tension in the circuit. This causes the stored energy device 86 to release its energy, typically in the form of movement to cause a distinct physical sensation to the wearer. The release can be instantaneous or can occur over a short period of time.

In one aspect of the present disclosure not shown, the transformational string 92 can be wrapped in an encasing material made from soft, flexible, and porous material such as film or a woven/nonwoven material. In this aspect, there is no extensive attachment of the transformational string 92 to the encasing material and the transformational string 92 is free to slide along the inside of the encasing. This encasing material typically allows fluid to distribute rapidly from the cover to the transformational string 92 in the event of a surface gush; or from the absorbent assembly 60 to the transformational string 92 during a capacity overload resulting in rewet.

The use of film or woven/nonwoven materials allows for fluid distribution and flexibility. This minimizes the feeling of stiffness and discomfort to the wearer. The location of the string with respect to the edge of the absorbent article 10 can be any value ranging from 0 to 45 mm but it is preferred that the string is located 10 to 20 mm from the edge. Another purpose of the encasing material is to protect the transformational string 92 from the construction hot melt adhesive that can glue the transformational string 92 to the absorbent article 10 and restrict the movement of the transformational string 92 after breakage.

In another aspect of the present disclosure, encasement guards (not shown) can be incorporated into the encasing at regular intervals along the transformational string 92 to reduce the influence of body weight on the transformational string 92. The influence of body weight can result in less effective triggering of the system. The guards can be made from a single material or a combination of materials such as silicone, plastic, rubber, paper, foam, sponge, gel, metal, etc. Any form of encasing can be used to increase the performance efficiency of the transformational string system.

In one aspect, the stored energy device 86 is connected to the transformational string 92 and is held in place at the back end of the absorbent article 10. In alternative aspects of the present disclosure illustrated in FIGS. 4A-5B, the stored energy device 86 includes one or more components 94 of an elastic nature that remain in an un-activated state prior to release by the breaking of the transformational string 92. The elastic potential energy stored in the stored energy device 86 is only activated when tension in the transformational string 92 is lost at any point in the circuit. The stored energy device 86 is then free to go back to its original state; this process generates a physical sensation (or a series of physical sensations) felt by the wearer. The stored energy device 86 can be made from silicone, plastic, rubber, paper, foam, sponge, gel, metal, etc. into a variety of shapes, sizes, and designs.

There is no restriction with respect to where the stored energy device 86 is placed, although placing the stored energy device 86 at the rear region of the absorbent article 10 will generally give the stored energy device 86 more space for movement.

In another aspect of the present disclosure, the transformational string 92 is connected to more than one stored energy device 86. All the stored energy devices 86 are connected via the transformational string 92 and held in their un-activated states. When the transformational string 92 breaks at one or more locations, all or some of the stored energy devices 86 are activated. Alternatively, the release of one stored energy device 86 can promote the release of other stored energy devices 86 further along the circuit, resulting in a series of releases that could increase the physical sensation experienced by the wearer.

The absorbent assembly 60 is not limited to any shape or size. The transformational string circuit, including the PVA string encasing, and the stored energy device 86 are connected together and placed on the absorbent assembly 60. After the topsheet 64 is placed, there can be additional channel embossing, adhesive, stitching, or any other suitable fastening methods at both sides of the encasing to keep the encasing in place.

In one aspect of the present disclosure not shown, the stored energy device 86 is one or more silicone rubber elements that are normally in a curved form. The silicone rubber elements are stretched or held flat by the tension in the PVA string 92. Upon breaking or dissolution of the transformational string 92, tension in the silicone rubber elements is activated and the wearer feels the "popping" of the silicone rubber from the stretched and flat state into the arched shape.

Figure 5A:
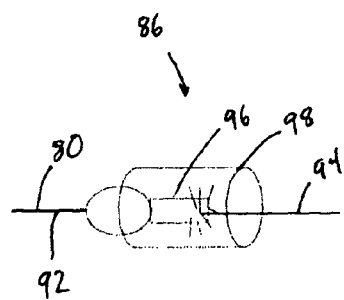
FIGS. 5A and 5B representatively illustrate schematic partial views of un-activated and activated alternative aspects of the stored energy device of FIG. 3.
Figure 5B:
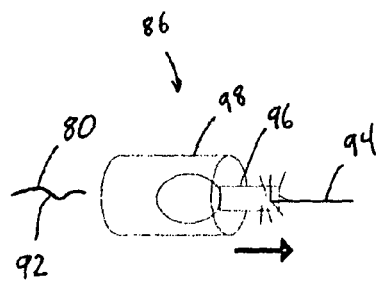

In another aspect of the present disclosure, the stored energy device 86 is a bristled object 96 elastically loaded into a protective tube 98 or other enclosure, as illustrated in FIGS. 5A and 5B, and held in place by the tension of the transformational string 92. Upon breaking or dissolution of the transformational string 92, tension in the bristled object 96 is released, the bristled object 96 is ejected from the tube 98 or other enclosure, and the wearer feels bristles on the bristled object 96. A cushion or bumper can be included to minimize the effects of body weight on the stored energy device 86. Such a cushion or other suitable spacing or cushioning element can be used in conjunction with any of the aspects described herein.

Figure 4A:
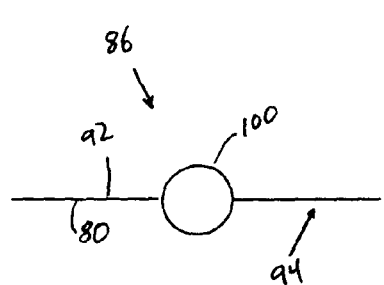
FIGS. 4A and 4B representatively illustrate schematic partial views of un-activated and activated aspects of the stored energy device of FIG. 3.
Figure 4B:
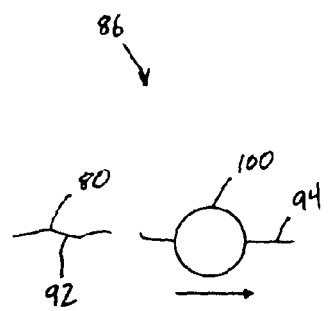

In another aspect of the present disclosure, the stored energy device 86 is a small solid object 100 such as a solid sphere attached to an elastic thread 94, as illustrated in FIGS. 4A and 4B, and held in place by the tension of the transformational string 92. Upon breaking or dissolution of the transformational string 92, tension in the elastic thread 94 is released, the solid object 100 moves in the direction of the elastic thread 94, and the wearer feels the movement of the solid object 100.

In alternative aspects of the present disclosure, any suitable stored energy device 86 can be used as long as it is safe and provides a physical sensation to the wearer upon breaking or dissolution of the transformational string 92. Stored energy devices 86 can use mechanical, electrical, electromechanical, chemical, some combination thereof, or any other form of stored energy provided it meets the requirements delineated herein.

In the aspect illustrated in FIGS. 1 and 2 in which the dimension change member 80 shortens upon exposure to menstrual fluid or other bodily exudate, the dimension change member 80 can include a water-shrinkable transformational string 92. The shrinkable transformational string 92 can be made from a modified-polyvinyl alcohol (PVA) material. Similar to that described above, a water-shrinkable transformational string 92 is placed near the perimeter 65 of the absorbent article 10. The transformational string 92 is connected to a signaling flap 88. When menstrual fluid or other bodily exudate contacts any point on the transformational string 92, the transformational string 92 shrinks and pulls open the signaling flap 88 to reveal signal material 90 underneath. The signal material 90 contacts the wearer's skin to warn of impending leakage. The signal material 90 must provide a noticeable and distinct yet comfortable physical sensation. Examples of suitable signal materials 90 include textured materials and materials that feel either hot or cold to the touch. In other aspects of the present disclosure, the signaling flap 88 itself provides the physical sensation to the wearer, and no signal material is necessary.

The transformational string 92, upon exposure to menstrual fluid or other bodily exudate, will shrink or shorten, thus increasing the tension in the transformational string 92 and increasing the influence of the transformational string 92 on the signaling flap 88. The transformational string 92 demonstrates shrinkage ability in both water (urine) and menstrual fluid. Shrinkage of up to approximately 40 percent by length is typical.

Suitable materials for the liquid shrinkable transformational string 92 include modified polyvinyl alcohol (PVA), modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid, carboxymethylcellulose and hydrolyzed acrylic fiber. In one particular aspect, a suitable modified PVA liquid shrinkable string can be obtained from Kuraray Group, Japan (www.kuraray.co.jp/en/) and Nitivy Company Limited, Japan (www.nitivy.co.jp/english/index.html).

When menstrual fluid or other bodily exudate contacts one or more points of the transformational string 92, the total length of the transformational string 92 reduces; this creates tension. The resulting tension pulls up the signaling flap 88. In the aspect illustrated in FIG. 1, the signaling flap 88 is located at the back of the absorbent article 10, although in other aspects the signaling flap 88 can be located at any suitable location including the front or the sides, or some combination thereof. In addition, two or more signaling flaps 88 can be used to provide alternative or additional sources of physical sensation when the transformational string 92 shortens.

Selected portions of the materials used in construction of the shrinkable string circuit can be adhered together using glue, embossing, stitching, or any other suitable means to form a guide for the shrinkable string circuit to stay in place. There should be little or no attachment of the transformational string 92 to both layers of porous materials such that the transformational string 92 can slide relatively freely along the guides formed by adhesive or embossing. Any suitable embossing, stitching, or adhesive coverage patterns can be applicable for this purpose.

By allowing the transformational string 92 to move freely, the shrinkable string shrinkage at any point will cause a significant reduction in length of the transformational string 92, not just mere puckering of absorbent article material. In one example, the signaling flaps 88 are located at both sides of the absorbent article 10, very close to the extension region. Upon sufficient fluid contact, the transformational string 92 shrinks, resulting in one or both signaling flaps 88 lifting. Only one end of each signaling flap 88 moves because the other end of the signaling flap 88 is affixed to the absorbent article 10 using adhesive, embossing, or any other suitable means.

In other aspects of the present disclosure, one or more lengths of transformational string 92 are placed between two layers of thin porous material to create a shrinkable string circuit. The circuit lies flat on or in the absorbent article and has one or more signaling flaps 88 located, for example, at both sides of the absorbent article 10, near the sides or extension regions. The signaling flaps 88 can include signal material 90 that provides a physical sensation to the wearer when her skin comes into contact with the signaling flaps 88.

In another aspect illustrated in FIG. 2, a concealment pocket 104 resides on one side, both sides, one end, or both ends of the absorbent article 10 to house the signaling flaps 88 prior to activation. Upon activation of the shrinkable string circuit by menstrual fluid or other bodily exudate, the transformational string 92 reduces in overall length, pulling each signaling flap 88 out of its pocket 104. The physical sensation felt by the wearer is translated into the message that the absorbent article 10 needs to be changed soon to prevent a leak from occurring. In addition, each signaling flap 88 can include an embossed line or other suitable structure at its base to facilitate movement of the signaling flap 88.

For the aspects in which the signaling flaps 88 themselves provide a physical sensation to the user, there is a need to contain the signaling flaps 88 to prevent a premature physical sensation to the wearer. In these aspects, concealment pockets 104 can be used and can be made from film, woven/nonwoven material, etc. Such concealment pockets 104 typically do not cover the entire absorbent article 10, but reside only the side(s) or end(s) of the absorbent article 10. If on the sides of the absorbent article 10, the pockets 104 will be in the vicinity of the extensions. The concealment pockets 104 are sized sufficiently to hide the signaling flaps 88.

In other aspects, the signaling flaps 88 can be located at other locations on the absorbent article such as the front and/or back of the absorbent article 10.

The signaling flaps 88 can include any suitable materials and structures that provide a sufficient physical sensation to the wearer when her skin touches the signaling flaps 88. Suitable materials for the signaling flaps 88 include one or more of brush filaments, textured nonwoven, cooling or warming materials, and three-dimensional structures.

With respect to assembly, an absorbent article 10 including such concealment pockets 104 can be made in many ways. In one example, it is important to determine the exact dimension of the concealment pockets 104 because incorrect dimensions might result in premature sensation or even non-activation.

The various layers of the absorbent article 10 are held together using construction hot melt adhesive or by any other suitable method. The transformational string 92 and signaling flaps 88 are connected together between two thin layers of material and adhered at selective areas to keep them in place at all times. The string/flap construction is positioned on the base absorbent article and side covers are applied to hide the signaling flaps 88 from the wearer before fluid activation of the system.

In another aspect of the present disclosure, the concealment pockets 104 are omitted and the signaling flaps 88 include signaling material 90.

In use, the leakage warning element 20 in the absorbent article 10 is designed to draw the wearer's attention to the fact that the absorbent assembly 60 is nearing fullness. The leakage warning element 20 is placed within the absorbent article 10 so that menstrual fluid or other body exudates contacts the dimension change member 80 once the absorbent assembly 60 approaches fullness. Once contacted by menstrual fluid or other bodily exudate, the leakage warning element 20 will produce a physical sensation. As a result, the wearer will experience that physical sensation when the absorbent assembly 60 is approaching fullness to indicate to the wearer that potential leakage is imminent.

Aspects of the disclosure have been described with reference to various specific and illustrative aspects and techniques. However, it should be understood that many variations and modifications can be made while remaining within the spirit and scope. Accordingly, this is intended to embrace all such alternatives, modifications and variations that fall within the spirit and scope of the appended claims. As various changes could be made in the above constructions and methods, without departing from the scope of the disclosure, it is intended that all matter contained in the above description and shown in the accompanying drawings shall be interpreted as illustrative and not in a limiting sense.

When introducing elements of the disclosure or the preferred aspect(s) thereof, the articles "a", "an", "the" and "said" are intended to mean that there are one or more of the elements. The terms "comprising," "including," and "having" are intended to be inclusive and mean that there can be additional elements other than the listed elements.

What is claimed is:

1. An absorbent article for preventing leakage, the article comprising:
    an absorbent assembly having an absorbent assembly perimeter, a longitudinal axis, and a transverse axis, wherein the longitudinal axis is perpendicular to the transverse axis and is centered between the intersections of the transverse axis and the assembly perimeter; and
    a leakage warning element disposed adjacent a portion of the perimeter, wherein the leakage warning element includes a dimension change member disposed only adjacent a portion of the perimeter and spaced apart from the longitudinal axis and adapted to dimensionally change upon liquid contact to produce a transition in the absorbent article between an activated state and an un-activated state, thereby producing a physical sensation indicating a fullness level of the absorbent assembly.

2. The article of claim 1, wherein the dimensional change is a breaking.

3. The article of claim 1, wherein the dimensional change is a shortening.

4. The article of claim 1, wherein the dimensional change member includes polyvinyl alcohol.

5. The article of claim 1, wherein the activated state includes a translation of a portion of the absorbent article.

6. The article of claim 5, wherein the portion of the absorbent article is a signaling flap.

7. The article of claim 5, wherein the translation uncovers a signal material.

8. The article of claim 5, wherein the signaling flap includes a signal material.

9. The article of claim 5, further comprising a pocket, wherein the signaling flap is disposed within the pocket when the absorbent article is in the un-activated state.

10. The article of claim 9, wherein the absorbent article further includes an extension, and wherein the pocket is disposed adjacent the extension.

11. The article of claim 1, wherein the leakage warning element includes a stored energy device.

12. The article of claim 11, wherein the stored energy device includes a spring.

13. The article of claim 1, wherein the absorbent assembly has a lateral edge, and wherein the portion of the perimeter is the lateral edge.

14. The article of claim 1, wherein the absorbent assembly has a longitudinal end, and wherein the portion of the perimeter is the longitudinal end.

15. The article of claim 1, the absorbent assembly has a longitudinal axis, and wherein the leakage warning element is spaced apart from the longitudinal axis.

16. The article of claim 1, the absorbent assembly has a transverse axis, and wherein the leakage warning element is spaced apart from the transverse axis.

17. The article of claim 1, wherein the article is a garment-like article including leg openings, and wherein the leakage warning element is disposed adjacent the leg openings.

18. An absorbent article for signaling imminence of leakage from the absorbent article, the article comprising:
- an absorbent assembly having an absorbent assembly perimeter, a longitudinal axis, and a transverse axis, wherein the longitudinal axis is perpendicular to the transverse axis and is centered between the intersections of the transverse axis and the assembly perimeter; and
- a leakage warning element including a signaling flap and a dimension change member, the dimension change member spaced apart from the longitudinal axis and disposed only along a portion of the perimeter, wherein the dimension change member is adapted to shorten upon liquid contact to produce a transition in the leakage warning element from an un-activated state to an activated state, thereby producing a physical sensation indicating that leakage is imminent from the absorbent assembly.

19. The article of claim 18, wherein the transition uncovers a signal material.

* * * * *